(12) United States Patent
Gilbert (10) Patent No.: US 9,534,647 B2
(45) Date of Patent: Jan. 3, 2017

(54) TORQUE LIMITING CLUTCH FOR ORTHOTIC AND PROSTHETIC DEVICES

(71) Applicant: B-TEMIA INC., Québec (CA)

(72) Inventor: Benoît Gilbert, Québec (CA)

( * ) Notice: Subject to any disclaimer, the term of this patent is extended or adjusted under 35 U.S.C. 154(b) by 267 days.

(21) Appl. No.: 14/387,218

(22) PCT Filed: Mar. 21, 2013

(86) PCT No.: PCT/CA2013/000268
§ 371 (c)(1),
(2) Date: Sep. 22, 2014

(87) PCT Pub. No.: WO2013/138912
PCT Pub. Date: Sep. 26, 2013

(65) Prior Publication Data
US 2015/0018970 A1    Jan. 15, 2015

Related U.S. Application Data (60) Provisional application No. 61/614,678, filed on Mar. 23, 2012, provisional application No. 61/642,031, filed on May 3, 2012.

(51) Int. Cl.
| | | |
|---|---|---|
| *F16D 49/10* | (2006.01) | |
| *F16D 65/14* | (2006.01) | |
| *A61F 2/68* | (2006.01) | |
| *A61F 2/50* | (2006.01) | |
| *A61F 5/01* | (2006.01) | |

(52) U.S. Cl.
CPC ............... *F16D 49/10* (2013.01); *A61F 2/50* (2013.01); *A61F 2/68* (2013.01); *A61F 5/0102* (2013.01); *F16D 65/14* (2013.01); *A61F 2002/6818* (2013.01); *A61F 2002/6845* (2013.01); *A61F 2005/0155* (2013.01)

(58) Field of Classification Search
CPC .................. A61F 5/0123; A61F 5/0125; A61F 2005/0139; A61F 5/0102; A61F 2005/0167; A61F 5/0111; A61F 5/0127; A61F 5/0195; A61F 2/54; A61F 2/60; A61F 5/01; F16D 49/10; F16D 65/06; F16D 65/18
See application file for complete search history.

(56) References Cited

U.S. PATENT DOCUMENTS 8,211,042 B2 *   7/2012   Gilbert ..................... A61F 2/64
                                                                602/16

* cited by examiner

*Primary Examiner* — Ophelia A Hawthorne
(74) *Attorney, Agent, or Firm* — Equinox IP; Christian Robillard (57) ABSTRACT

A torque limiting assembly for use with an actuator having a torque transfer output, the assembly comprising a brake pad, a band connected at a first extremity to a first extremity of the brake pad and a cam linking a second extremity of the band to a second extremity of the brake pad. The brake pad and the band are configured to wrap around the a torque transfer output and the positioning of the cam in a first position frictionally engages the brake pad and the band with the a torque transfer output while the positioning of the cam in a second position disengages the brake pad and the band with the a torque transfer output.

20 Claims, 6 Drawing Sheets

TORQUE LIMITING CLUTCH FOR ORTHOTIC AND PROSTHETIC DEVICES

CROSS-REFERENCE TO RELATED APPLICATIONS

This application claims the benefits of U.S. provisional patent applications Nos. 61/613,678 and 61/642,031, filed on Mar. 21, 2012 and May 3, 2012, respectively, which are herein incorporated by reference.

TECHNICAL FIELD

The present disclosure relates to a torque limiting clutch for orthotic and prosthetic devices.

BACKGROUND

Rotating systems can have enough rotating energy (i.e. inertia) to cause significant machine damage during a jam-up or system crash. This inertia varies based on the RPM and rotating mass for each application. A high mass low speed application could do more damage than a low mass high speed one during a crash. In order to prevent damage, a torque limiter, which is basically a mechanical fuse, is used to shut down the machine and allow the rotating energy to dissipate without causing excessive damage.

Different types of torque limiters are currently being used in the industry, namely disconnect, shear pin, synchronous magnetic, ball detent, pawl and spring, etc.

The only type of torque limiters that allow for the dissipation of rotation energy through friction is the disconnect types (i.e. torque limiting clutches) who "wait" for the torque to diminish to a predetermined level before reengaging.

The main limitations with the existing disconnect type torque limiters are that they are cumbersome (vs. torque capacity) and typically cannot be engaged or disengaged manually. Furthermore, they do not actively dissipate rotational energy.

Accordingly, there is a need for a torque limiting clutch that is compact, can be engaged or disengaged manually and dissipates rotational energy.

SUMMARY

The present disclosure provides a torque limiting assembly for use with an actuator having a torque transfer output, the assembly comprising:
a brake pad;
a band connected at a first extremity to a first extremity of the brake pad; and
a cam linking a second extremity of the band to a second extremity of the brake pad;
wherein the brake pad and the band are configured to wrap around the torque transfer output and whereby the positioning of the cam in a first position frictionally engages the brake pad and the band with the torque transfer output, and positioning of the cam in a second position disengages the brake pad and the band with the torque transfer output.

There is also provided a torque limiting assembly as described above, further comprising a tension adjustment mechanism connecting the first extremity of the band to the first extremity of the brake pad, wherein the tension adjustment mechanism is configured so as to augment or diminish the frictional engagement of the brake pad and the band with the torque transfer output when the cam is in the first position.

There is further provided a torque limiting assembly as described above, further comprising a liner positioned on a surface of the band and/or the brake pad that is in frictional engagement with the torque transfer output when the cam is in the first position, in one or more embodiments the liner is made of a material having a high friction coefficient and/or wear resistant and/or compressible.

There is still further provided a torque limiting assembly as described above, wherein the cam is composed of two eccentric baring surfaces off center with regard to one another.

There is also provided actuated orthotic device, comprising:
a proximal and a distal brace structures for attachment to a limb of a user;
an actuator operatively connecting the proximal and the distal brace structures, the actuator including a torque transfer output connected to one of the proximal and the distal brace structures to impart movement to the limb of the user; and
a torque limiting assembly as described above, positioned around the torque transfer output, the torque limiting assembly limiting the maximum force exerted on the user.

BRIEF DESCRIPTION OF THE FIGURES

Embodiments of the disclosure will be described by way of examples only with reference to the accompanying drawings, in which.

DETAILED DESCRIPTION

Generally stated, the non-limitative illustrative embodiment of the present disclosure provides a torque limiting clutch consisting in a band brake mechanism for an actuator that starts slipping when the torque is higher than a preset torque. The torque limiting clutch serves to:
protect the actuator (transmission, motor and other mechanical components) from external high impact shocks;
protect the actuator from inertial loads when the actuator is hitting a travel extension limit (hard stop) at high speed. In this case extreme loads can occur if the kinetic energy is not dissipated somewhere; and
protect the environment from high forces that could be exerted by the actuator.

Another feature of the torque limiting clutch is to allow manual disengagement of the actuator in case of malfunction of the actuator or power failure.

Figure 1:
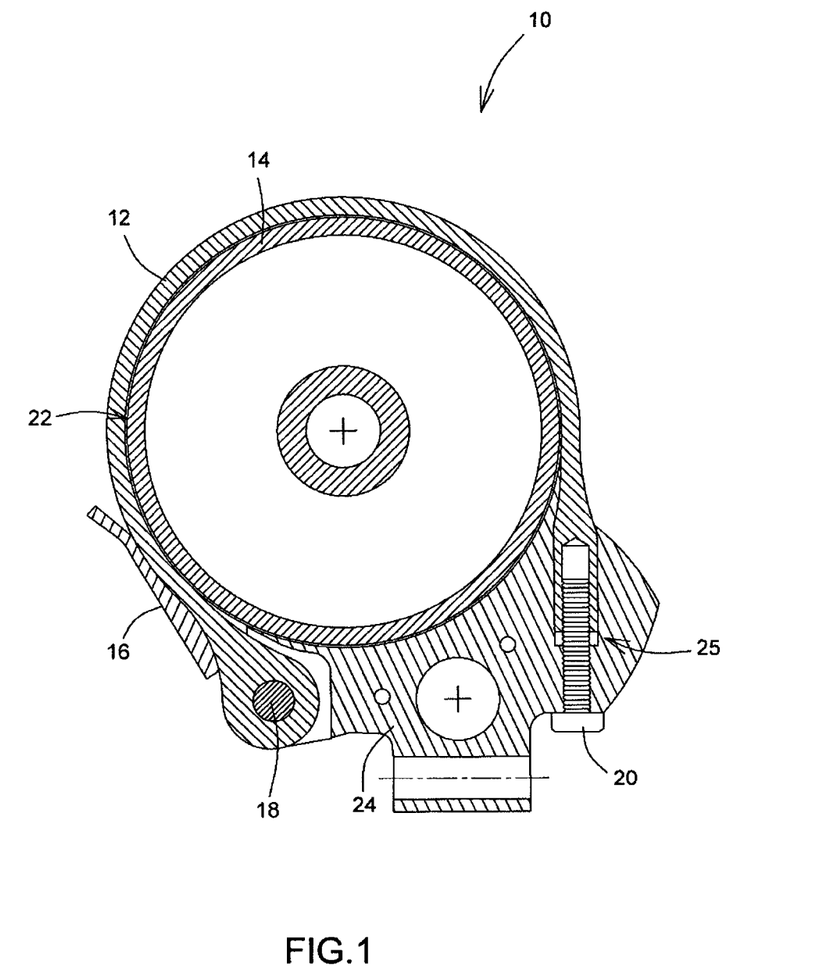
FIG. 1 is a cross-sectional view of the torque limiting clutch in accordance with an illustrative embodiment of the present disclosure.
Figure 2:
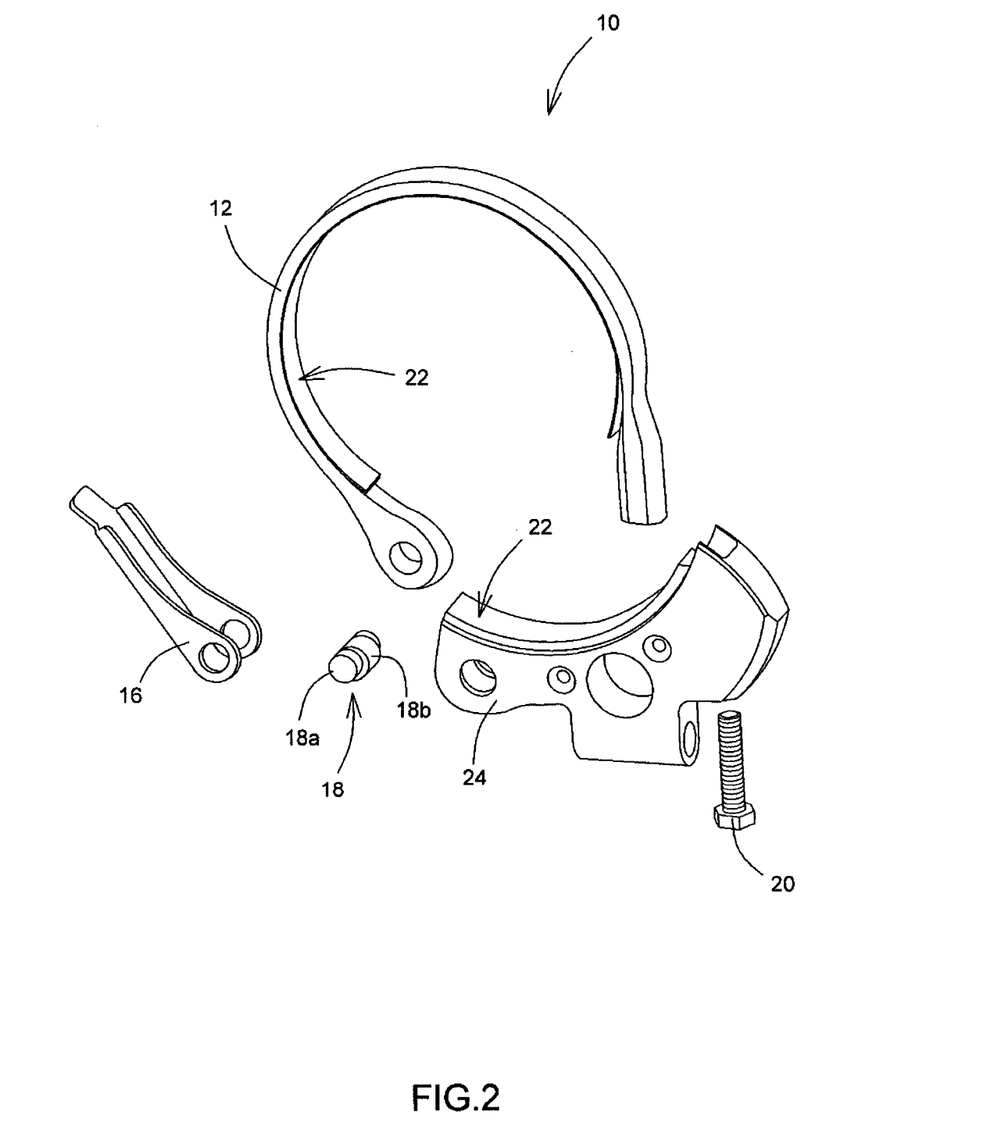
FIG. 2 is an exploded view of the torque limiting clutch.

Referring to FIGS. 1 and 2, the torque limiting clutch 10 consists of a band 12 that is wrapped partly around an actuator torque transfer output, which in the illustrative embodiment is a rotating drum 14, and a brake pad 24. It is to be understood that the torque transfer output could be another rotating mechanism such as, for example, a rotating shaft. Tension can be applied to the band 12 using, for example, a lever 16 attached to a cam 18 linking the band 12 to a first extremity of the brake pad 24. It is to be understood that mechanisms other than a lever 16 may be used to operate the cam 18. The tension can be adjusted using a tension adjustment mechanism here in the form of a screw 20 operatively connecting the band 12 to a second extremity of the brake pad 24, wherein rotation of the crew 20 in a first direction pulls the band 12 into a cavity 25 within the brake pad 24, therefore augmenting the frictional engagement of the brake pad 24 and the band 12 with the rotary drum 14 rotation the opposed direction allows the band 12 to pull out of the cavity 25, therefore diminishing the frictional engagement of the brake pad 24 and the band 12 with the rotary drum 14. A liner 22, for example made of a high friction material, serves as a friction surface. The liner 22 is advantageously wear resistant and somewhat soft or compressible in order to "encapsulate" any dirt or particles that may be trapped between the band 12, the brake pad 24 and the rotating drum 14. The band 12, the brake pad 24 and the rotating drum 14 are advantageously made from the same material, for example Alu 7075-T6, to ensure that the braking force does not change significantly when the temperature fluctuates due to, for example, thermal expansion. The rotating drum 14 may be, for example, hard anodized (i.e. type II, 50 μm) for wear resistance.

Figure 3A:
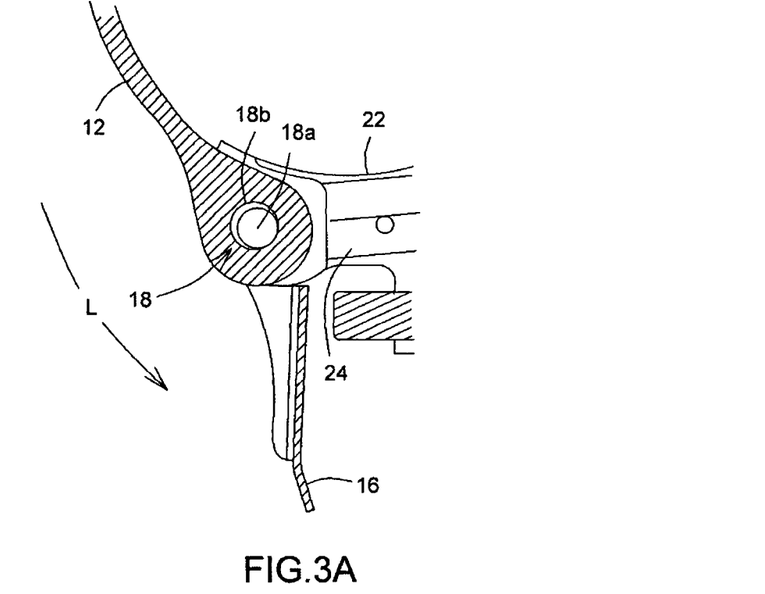
FIG. 3 is a cross-sectional view of the lever and cam of the torque limiting clutch.
Figure 3B:
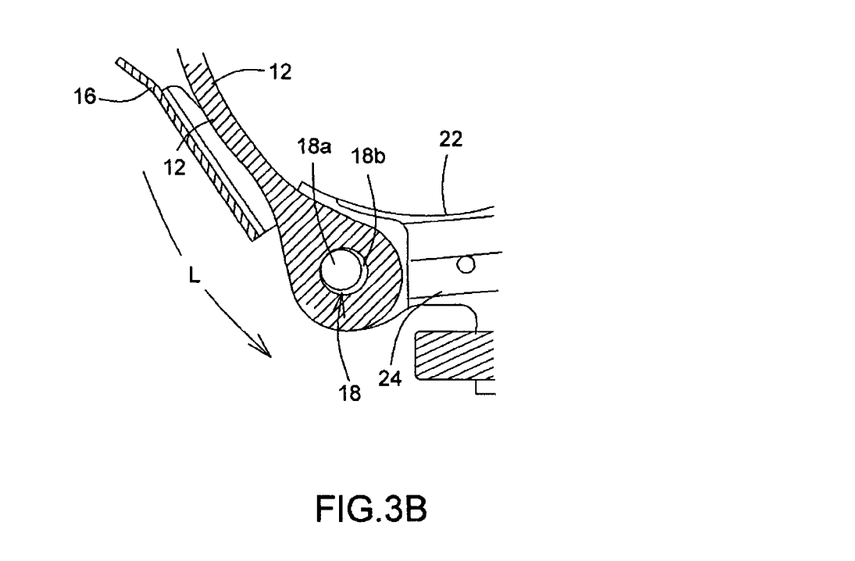

The torque limiting clutch 10 can be disengaged, for example by lifting in direction "L" the lever 16 (see FIG. 3), positioning the cam (18) in a position that allows for completely free motion of the rotating drum 14. The torque limiting clutch 10 can be disengaged in case of, for example, malfunction or power failure.

The cam 18 provides the tension in the band 12 when the lever 16 is engaged. The cam 18 is designed with two eccentric bearing surfaces 18a and 18b (best seen in FIGS. 2 and 3) that are off center with regard to one another. After assembly, the lever 16 is advantageously micro-welded onto the cam 18 thus making them unitary. The tension adjustment mechanism, i.e. screw 20, is used to adjust the band 12 tension in order to get the desired braking torque.

Figure 4:
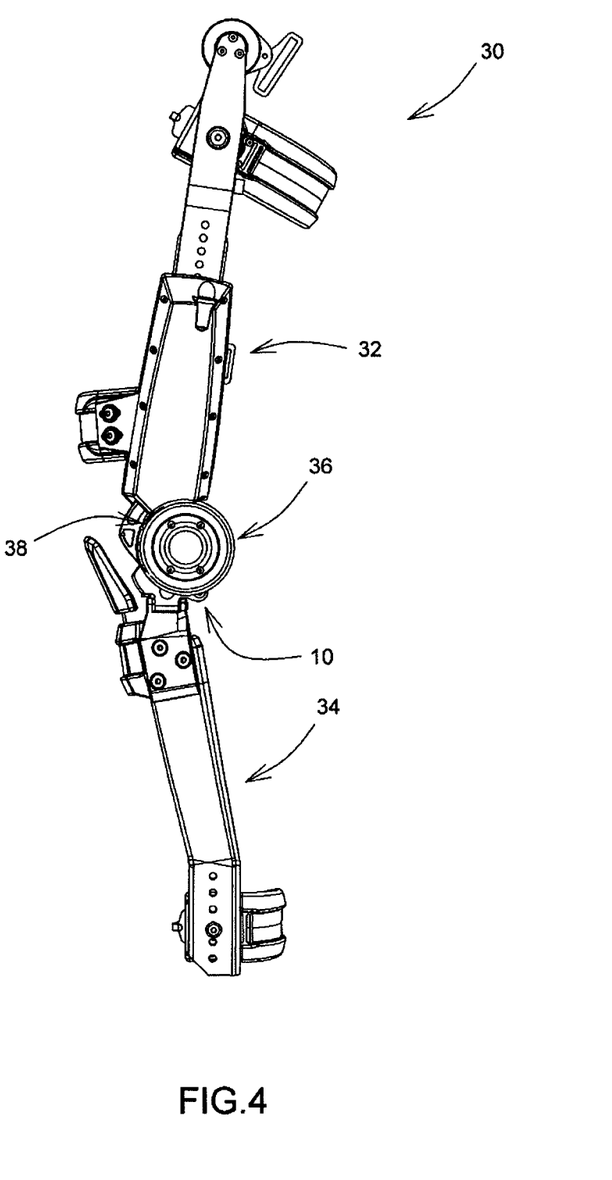
FIG. 4 is a side view of an actuated orthotic device integrating the torque limiting clutch.
Figure 5:
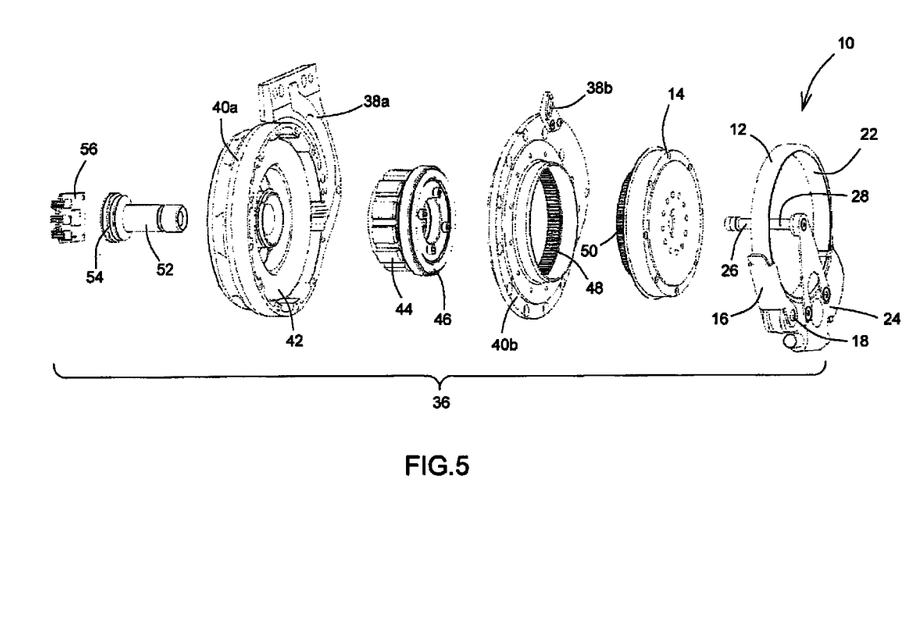
FIG. 5 is an exploded perspective view of the actuator of the actuated orthotic device of FIG. 4.

Referring now to FIGS. 4 and 5, there is shown an illustrative example of the torque limiting clutch 10 integrated with an actuated orthotic device 30 having proximal 32 and distal 34 brace structures for attachment to the limb of a user. The proximal 32 and distal 34 brace structures are operatively linked together via an actuator 36 designed to impart movement to the limb of the user. The torque limiting clutch 10 is located inside the housing of the actuator 36 and ensures that the actuator 36, as well as the other components of the orthotic device 30 (i.e. brace structures 32 and 34, torque sensor 38, etc.) are not damaged by external shocks, such as when the user lands after a jump, or when the orthotic device 30 reaches its extension limit. Furthermore, the torque limiting clutch 10 limits the maximum force exerted on the user, thus reducing the risk of injury in the event of shocks.

Referring to FIG. 5, the actuator 36 comprises a housing assembly 40a, 40b for holding the various components of the actuator 36, namely the torque sensor beam 38a, configured to be connected to the brace structure 32, the torque sensor magnet 38b, the motor stator 42 and rotor 44, the transmission wave generator 46, the transmission circular spline 48, the rotating drum 14 with transmission flex spline 50, the center shaft 52 with conical bearings 54, and the angle sensor 56. In the present illustrative embodiment, the torque limiting clutch 10 further comprises an angle sensor magnet 26 mounted on a shaft 28 supported by the brake pad 24. The brake pad 24 being configured to be connected to the distal brace structure 34, the angle sensor magnet 26 and the angle sensor 56 cooperate together in order to provide a measure of the angle between the proximal 32 and distal 34 brace structures.

Braking Force and Stress

Figure 6:
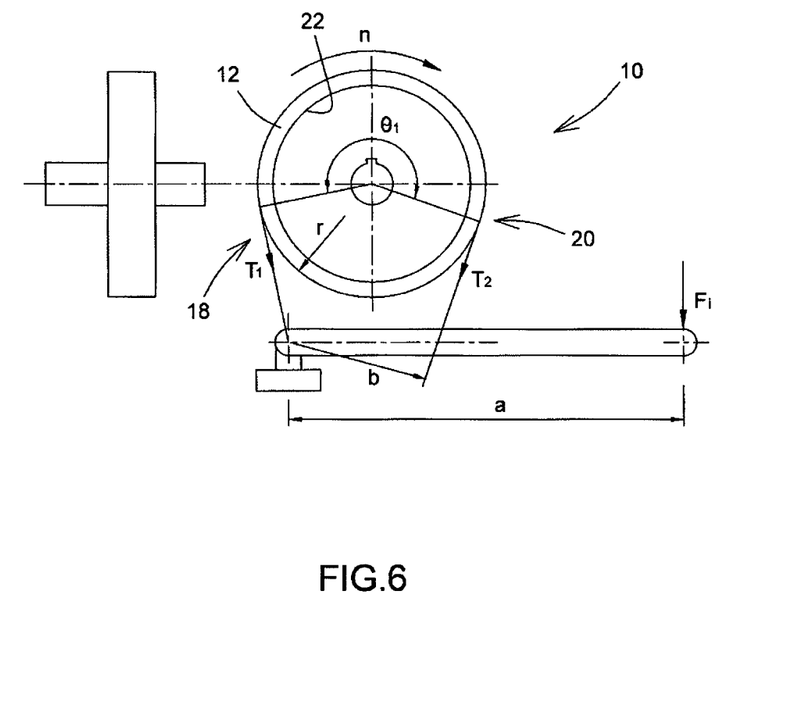
FIG. 6 is a conceptual representation of the torque limiting clutch for the computation of its braking force and the stress in its various components.

Referring to FIG. 6, there is shown a conceptual representation for the computation of the braking force of the torque limiting clutch 10 and the stress in its various components for the above described illustrative example.

Equation 1 illustrates the relation between band 12 tensions, coefficient of friction of the liner 22 and wrapping angle:

$$T_1/T_2 = e^{\mu \theta_t} \qquad \text{Equation 1}$$

where:
 $T_1$ and $T_2$ are the tension forces;
 $\mu$ is the friction coefficient of the liner 22;
 $\theta_t$ is the wrapped angle of the band 12.

In the illustrative embodiment of FIGS. 4 and 5, the desired braking torque capability is established at 75 Nm, although the desired braking force is of 50 Nm. It is to be noted that the brake pad 24 to which is attached the band 12 also provides a braking force. The total force applied on the brake pad 24 being roughly $T_1+T_2$, we find the total braking torque to be:

$$\text{Torque} = (T_2 - T_1) \times D/2 + \mu(T_2 + T_1) \times D/2 \qquad \text{Equation 2}$$

Using Equations 1 and 2 with $\theta_1 220°$, $\mu=0.1$, D=0.065 m (where D is the diameter of the rotating drum 14) and Torque=75 Nm, we find the following tensions in the band:

$$T_1 = 4987 N$$

$$T_2 = 3571 N$$

In the illustrative example, the cam 18 is designed with two eccentric bearing surfaces 18a and 18b (best seen in FIGS. 2 and 3) that are off center by 0.5 mm. The stress level in the band 12 area is of about 200 MPa, while the stress in the cam 18 area is up to about 315 MPa. Considering that the band 12 is not submitted to a large amount of cycles, this stress level is considered acceptable. Assuming the maximum stress to be 350 MPa and the minimum stress to be 0 MPa, it can be estimated that the band 12 can resist at least 50 K engaging/disengaging cycles.

The average pressure on the liner 22 is found to be of about 16 MPa (with the band 12 width being of 8 mm). This pressure level is acceptable for the use of, for example, Acetal plastic which has a limit of 70 MPa.

The tension stress in the adjustment screw 20 is computed at 580 MPa. The stress level in the adjustment screw 20 being important, a screw with a grade of at least 8.8 is recommended.

The above calculations were calculated using a finite element analysis.

In the illustrative example, the linear displacement of the extremity of the band 12 being of 0.18 mm and the deformation of the rotating drum 14 providing a dimensional change of the same order of magnitude, the cam 18 must provide sufficient travel to compensate for the extension of the band 12 and compression of the rotating drum 14 in order to engage and disengage efficiently.

It is to be understood that the various materials, values and measurements of the components of the torque limiting clutch 10 have been described in accordance with an illustrative embodiment of the present disclosure and that these may vary depending, for example, on the specific application.

It is further to be understood that the torque limiting clutch 10 may be adapted for applications other than orthotic and prosthetic devices without departing from the scope of the present disclosure.

Although the present disclosure has been described with a certain degree of particularity and by way of an illustrative embodiments and examples thereof, it is to be understood that the present disclosure is not limited to the features of the embodiments described and illustrated herein, but includes all variations and modifications within the scope and spirit of the disclosure as hereinafter claimed.

What is claimed is:

1. A torque limiting assembly (10) for use with an actuator having a torque transfer output (14), the assembly comprising:
   a brake pad (24);
   a band (12) connected at a first extremity to a first extremity of the brake pad (24); and
   a cam (18) linking a second extremity of the band (12) to a second extremity of the brake pad (24);
   wherein the brake pad (24) and the band (12) are configured to wrap around the torque transfer output (14) and whereby the positioning of the cam (18) in a first position frictionally engages the brake pad (24) and the hand (12) with the torque transfer output (14), and positioning of the cam (18) in a second position disengages the brake pad (24) and the band (12) with the torque transfer output (14).

2. The torque limiting assembly (10) of claim 1, further comprising a liner (22) positioned on a surface of the band (12) that is in frictional engagement with the torque transfer output (14) when the cam (18) is in the first position.

3. The torque limiting assembly (10) of claim 2, wherein the band liner (22) is made of a material having a high friction coefficient.

4. The torque limiting assembly (10) of claim 3, wherein the hand liner (22) material is wear resistant.

5. The torque limiting assembly (10) of claim 3, wherein the band liner (22) material is compressible, thereby encapsulating dirt particles trapped between the band (12) and the torque transfer output (14).

6. The torque limiting assembly (10) of claim 1, further comprising a liner (22) positioned on a surface of the brake pad (24) that is in frictional engagement with the torque transfer output (14) when the cam (18) is in the first position.

7. The torque limiting assembly (10) of claim 6, wherein the brake pad liner (22) is made of a material having a high friction coefficient.

8. The torque limiting assembly (10) of claim 7, wherein the brake pad liner (22) material is wear resistant.

9. The torque limiting assembly (10) of claim 7, wherein the brake pad liner (22) material is compressible, thereby encapsulating dirt particles trapped between the brake pad (24) and the torque transfer output (14).

10. The torque limiting assembly (10) of claim 1, further comprising a tension adjustment mechanism (20) connecting the first extremity of the band (12) to the first extremity of the brake pad (24), wherein the tension adjustment mechanism (20) is configured so as to augment or diminish the frictional engagement of the brake pad (24) and the band (12) with the torque transfer output (14) when the cam (18) is in the first position.

11. The torque limiting assembly (10) of claim 10, wherein the tension adjustment mechanism comprises a screw (20) operatively connecting the first extremity of the band (12) to the first extremity of the brake pad (24), wherein rotation Of the crew (20) in a first direction pulls the first extremity of the band (12) into a cavity (25) within the brake pad (24) therefore augmenting the frictional engagement of the brake pad (24) and the band (12) with the torque transfer output (14) when the cam (18) is in the first position, and rotation of the crew (20) in a second direction allows the first extremity of the band (12) to pull out of the cavity (25) therefore diminishing the frictional engagement of the brake pad (24) and the band (12) with the torque transfer output (14) when the cam (18) is in the first position.

12. The torque limiting assembly (10) of claim 1, further comprising a lever (16) attached to the cam (18).

13. The torque limiting assembly (10) of claim 12, wherein the cam (18) and the lever (16) are unitary.

14. The torque limiting assembly (10) of claim 1, wherein the cam (18) is composed of two eccentric baring surfaces (18a, 18b) off center with regard to one another.

15. The torque limiting assembly (10) of claim 1, wherein the torque transfer output (14) is a rotating drum.

16. An actuated orthothic device (30), comprising:
    a proximal (32) and a distal (34) brace structures for attachment to a limb of a user;
    an actuator (36) operatively connecting the proximal (32) and the distal (34) brace structures, the actuator (36) including a torque transfer output (14) connected to one of the proximal (32) and the distal (34) brace structures to impart movement to the limb of the user; and
    a torque limiting assembly (10) in accordance with claim 1 positioned around the torque transfer output (14), the torque limiting assembly (10) limiting the maximum force exerted on the user.

17. The actuated orthothic device (30) of claim 16, wherein the torque limiting assembly (10) further comprises a tension adjustment mechanism (20) connecting the first extremity of the band (12) to the first extremity of the brake pad (24), wherein the tension adjustment mechanism (20) is configured so as to augment or diminish the frictional engagement of the brake pad (24) and the band (12) with the torque transfer output (14) when the cam (18) is in the first position.

18. The actuated orthothic device (30) of claim 17, wherein the tension adjustment mechanism comprises a screw (20) operatively connecting the first extremity of the band (12) to the first extremity of the brake pad (24), wherein rotation of the crew (20) in a first direction pulls the first extremity of the band (12) into a cavity (25) within the brake pad (24) therefore augmenting the frictional engagement of the brake pad (24) and the band (12) with the torque transfer output (14) when the cam (18) is in the first position, and rotation of the crew (20) in a second direction allows the first extremity of the band (12) to pull out of the cavity (25) therefore diminishing the frictional engagement of the brake pad (24) and the band (12) with the torque transfer output (14) when the cam (18) is in the first position.

19. The actuated orthothic device (30) of claim 16, wherein the actuator (36) includes a housing assembly (40a, 40b) for holding torque transfer output (14) and the torque limiting assembly (10).

20. The actuated orthothic device (30) of claim 16, wherein the cam (18) is composed of two eccentric baring surfaces (18*a*, 18*b*) off center with regard to one another.

* * * * *